United States Patent
Srivastava et al.

(10) Patent No.: US 10,954,630 B2
(45) Date of Patent: Mar. 23, 2021

(54) PROCESS FOR PRODUCING CELLULOSE WITH LOW IMPURITIES FROM SUGARCANE BAGASSE

(71) Applicant: GODAVARI BIOREFINERIES LTD., Maharashtra (IN)

(72) Inventors: Sangeeta Srivastava, Maharashtra (IN); Ramesh Shettar, Maharashtra (IN); Rakesh Kumar Jain, Uttar Pradesh (IN); Ashwani Kumar Dixit, Uttar Pradesh (IN); Diwakar Pandey, Uttar Pradesh (IN)

(73) Assignee: GODAVARI BIOREFINERIES LTD., Maharashtra (IN)

( * ) Notice: Subject to any disclaimer, the term of this patent is extended or adjusted under 35 U.S.C. 154(b) by 262 days.

(21) Appl. No.: 15/753,943

(22) PCT Filed: Aug. 19, 2016

(86) PCT No.: PCT/IN2016/050277
§ 371 (c)(1),
(2) Date: Feb. 20, 2018

(87) PCT Pub. No.: WO2017/029685
PCT Pub. Date: Feb. 23, 2017

(65) Prior Publication Data
US 2019/0010660 A1    Jan. 10, 2019

(30) Foreign Application Priority Data
Aug. 19, 2015  (IN) .................. 3151/MUM/2015

(51) Int. Cl.
| | |
|---|---|
| *D21C 3/02* | (2006.01) |
| *D21C 5/00* | (2006.01) |
| *D21C 9/10* | (2006.01) |
| *C12N 9/24* | (2006.01) |

(52) U.S. Cl.
CPC ............. *D21C 5/005* (2013.01); *C12N 9/248* (2013.01); *D21C 3/02* (2013.01); *D21C 3/022* (2013.01); *D21C 5/00* (2013.01); *D21C 9/10* (2013.01)

(58) Field of Classification Search
USPC ........................................... 162/16
IPC ......................... D21C 5/005,3/02, 3/022, 9/10
See application file for complete search history.

(56) References Cited

U.S. PATENT DOCUMENTS

| | | |
|---|---|---|
| 7,156,952 B2 | 1/2007 | Ragnar et al. |
| 2012/0111514 A1* | 5/2012 | Dottori ............. C13K 1/02 162/68 |
| 2012/0316330 A1 | 12/2012 | Zhu et al. |
| 2015/0166683 A1 | 6/2015 | Haan et al. |

FOREIGN PATENT DOCUMENTS

WO    WO 2012/070072 A2    5/2012

OTHER PUBLICATIONS

International Search Report, dated Mar. 31, 2017 for corresponding International Application No. PCT/IN2016/050277.
Written Opinion of ISA, dated Mar. 31, 2017 for corresponding International Application No. PCT/IN2016/050277.

* cited by examiner

*Primary Examiner* — Jacob T Minskey
(74) *Attorney, Agent, or Firm* — Intellectual Property Law Group LLP

(57) ABSTRACT

The present invention relates to a process for producing cellulose with low inorganic impurities from sugarcane bagasse, the process comprising treating prehydrolysed sugarcane bagasse with a mixture of sulfite and at least one alkali to obtain residue having undissolved cellulose along with lignin rich liquor. The residue having undissolved cellulose is further subjected to delignification and addition of at least one enzyme to obtain a cellulose rich pulp. The cellulose rich pulp obtained is then treated with bleaching agents followed by separating pure cellulose rich pulp having high a-cellulose content and low inorganic impurities.

7 Claims, No Drawings

PROCESS FOR PRODUCING CELLULOSE WITH LOW IMPURITIES FROM SUGARCANE BAGASSE

CROSS-REFERENCE TO RELATED APPLICATIONS

This application is a U.S. National Phase application, under 35 U.S.C. § 371, of International Application no. PCT/IN2016/050277, with an international filing date of Aug. 19, 2016, and claims benefit of India Application no. 3151/MUM/2015 filed on Aug. 19, 2015, and which are hereby incorporated by reference for all purposes.

FIELD OF THE INVENTION

The present invention relates to a process for producing cellulose almost free of inorganic impurities. More particularly, the present invention relates to a process for producing cellulose almost free of inorganic impurities from sugarcane bagasse.

BACKGROUND OF THE INVENTION

Cellulose of a good and desirable quality is primarily produced from wood, thus making wood the most widely and commonly used raw material for the production of cellulose. However, there is a shortage of this raw material due to depletion of forests worldwide and also due to many countries being deficient in forests. As a result of such shortage, there is a need to preserve the forests and hence explore alternate raw materials for the production of cellulose.

Further, cellulose based fibrous resources are mainly used by the paper industry. The demand for paper worldwide is so large that almost every possible source of cellulose based fibrous raw material is exploited by paper industry. Therefore, in order to ensure a sustained supply of cellulose, the cellulose based industry has been forced to explore and consider alternate raw materials such as non-woody cellulose containing fibrous raw materials for the production of cellulose. Non woody raw materials like bamboo, cereal straws, bagasse, are characterized by high silica content and higher hemicelluloses content.

Sugar mills generate nearly millions of tones of sugarcane bagasse annually. For every ton of sugar produced around 1.3-1.5 ton of dry bagasse is generated, thus making sugarcane bagasse a very prominent waste product of sugarcane. Thus, sugarcane bagasse a by product of the sugar industry is one such non-woody fibrous residue that is left behind after the juice has been extracted from sugarcane.

However, in spite of being a potential source of good quality cellulose and other value added chemicals, a major problem in using sugarcane bagasse even after the removal of pith as an alternate to wood is the presence of impurities which makes it undesirable for the production of good quality and high purity cellulose. Therefore, various studies have been conducted on the utilization of sugarcane bagasse in the production of high quality cellulose and for the production of high value added products such as microcrystalline cellulose or cellulose esters. Even for the production of such value added products there is a need of cellulose of a very high quality which is devoid of impurities such as silica. Indian Patent Application no. 3240/MUM/2010 relates to a process for producing cellulose with a high molecular weight wherein pretreated lignocellulosic material is treated with alkali, sulfite and anthraquinone for solubulising the lignin component by converting it to lignosulfonate. This is then followed by washing and screening the pulp followed by bleaching the washed pulp and separating the fibrous organic residue and washing the pulp to obtain 92% alpha cellulose having a high molecular weight. The cellulose obtained by the method disclosed in the aforementioned application does not however teach a method to reduce the level of impurities to obtain cellulose of a high quality. Further, in the aforementioned process hazardous chemicals such as anthraquinone is used.

Indian Patent Application No. 1893/DEL/2007 relates to a process for fractionation and isolation of high α cellulose pulp, hemicelluloses and lignin from depithed fibrous organic biomass comprising the steps of contacting the biomass with steam hydrolyzing and solubulising the hemicelluloses component, separating and washing the undissolved fibrous organic biomass with water, followed by treatment with an alkali and then mineral acid to precipitate the lignin. This is then followed by separating and washing the undissolved fibrous organic biomass, bleaching, separating, washing and drying the fibrous organic residue to obtain a pulp of α-cellulose. However, the method used does not indicate a process to remove the impurities of sugarcane bagasse to yield high quality cellulose.

Silica is present in a high quantity in the raw material and is distributed throughout the cell wall in such a way that for the conversion of the raw material to cellulosic material, it becomes difficult to efficiently remove the impurities by the known processes. Though the major portion of the silica dissolves during alkaline treatment of the fibrous raw material, a substantial portion still remains to the cellulosic product thereby hampering the purity of the final cellulosic product thus restricting the use of the final cellulosic product for the industrially useful product.

Thus, there is a need for a process to produce cellulose with low impurities from sugarcane bagasse.

SUMMARY OF THE INVENTION

An embodiment of the present invention relates to a process for producing cellulose with low inorganic impurities from sugarcane bagasse, the process comprising treating prehydrolysed sugarcane bagasse with a mixture of sulfite and at least one alkali to obtain residue having undissolved cellulose along with lignin rich liquor.

Another embodiment of the present invention relates to a process for producing cellulose with low impurities, the process comprising:
  prehydrolyzing sugarcane bagasse to obtain a residue;
  treating the residue with sulfite and at least one alkali to obtain residue having undissolved cellulose along with lignin rich liquor;
  subjecting the residue having undissolved cellulose to further delignification followed by addition of at least one enzyme to obtain a cellulose rich pulp;
  treating the cellulose rich pulp with bleaching agent to obtain pure cellulose rich pulp; and separating the pure cellulose rich pulp having high α-cellulose content.

Another embodiment of the present invention relates to a mixture for treatment of lignocellulose material, the mixture comprising sulfite and at least one alkali.

DETAILED DESCRIPTION OF THE INVENTION

The present invention relates to a process for producing cellulose almost free of impurities.

The present invention also relates to a process for producing cellulose and other useful product derivatives from sugarcane bagasse.

An embodiment of the present invention relates to a process for producing cellulose having more than 95% of α cellulose.

Another embodiment of the present invention relates to a process for producing cellulose having inorganic impurities such as potassium, chlorides, silica less than 0.05% preferably less than 0.03% most preferably less than 0.015% inorganic impurities Sugarcane bagasse residue produced as a waste product after removal of sugarcane juice is used in the present invention. Sugarcane bagasse contains pith which forms almost 30% or more of the total bagasse residue. In one embodiment of the present invention, sugarcane bagasse after removal of pith is used. Such sugarcane bagasse contains inorganic impurities around 2.5% w/w to 5% w/w and inorganic impurities even at this level is undesirable in order to produce cellulose of high quality capable of being useful in making of cellulose based products, other speciality chemicals and products. Accordingly, the present invention provides a process for producing cellulose almost free from inorganic impurities from sugarcane bagasse.

An embodiment of the present invention relates to a process for producing cellulose with low inorganic impurities from sugarcane bagasse, the process comprising treating prehydrolysed sugarcane bagasse with a mixture of sulfite and at least one alkali to obtain residue having undissolved cellulose along with lignin rich liquor.

The prehydrolysed sugarcane bagasse is obtained by treating the sugarcane bagasse residue with water in a ratio of 1:5 to 1:10 at a temperature in a range of 120° C.-170° C. preferably at 140° C.-160° C. for 60 to 215 minutes to obtain residue.

The prehydrolysed sugarcane bagasse is further treated with a mixture of sulfite and atleast one alkali. The sulfite is 5%-10% sodium sulfite, and the alkali is selected from 1%-4% sodium carbonate, 7%-8% sodium hydroxide or a mixture thereof preferably the alkali is a mixture of, sodium carbonate and sodium hydroxide and wherein the process is carried out at a temperature in the range of 140° C.-180° C. preferably 160° C.-180° C. for 30-130 minutes.

In the aforesaid embodiment, the residue having undissolved cellulose obtained is then subjected to delignification at a temperature in the range of 60° C.-140° C. at a pH of 10-11 in the presence of 2%-4% of sodium hydroxide and oxygen pressure at 3-5 kgs to obtain cellulose rich pulp.

Another embodiment of the present invention relates to a process for producing cellulose with low impurities, the process comprising of
prehydrolyzing sugarcane bagasse to obtain a residue;
treating the residue with sulfite and at least one alkali to obtain a residue having undissolved cellulose along with lignin rich liquor;
subjecting the residue having undissolved cellulose to delignification followed by addition of at least one enzyme to obtain a cellulose rich pulp;
treating the cellulose rich pulp with bleaching agent to obtain pure cellulose rich pulp; and separating the pure cellulose rich pulp having high α-cellulose content.

In the aforementioned embodiment, prehydrolysis of the sugarcane bagasse residue is carried out with water at a temperature in the range of 120° C.-170° C. preferably 140° C.-160° C. for 60-215 minutes and at a solid to liquid ratio of 1:5 to 1:10 which is then separated into 70%-80% of residue and more than 90% hemicelluloses having a concentration of more than 30g/l of xylan.

Prehydrolysis of sugarcane bagasse dissolves and separates the hemicelluloses portion in the form of xylan wherein the recovery is of around 90%. The solid and liquid portions obtained in the step of prehydrolysis are separated by vaccum filteration and further washing is carried out to recover maximum sugars.

Further, prehydrolysis of sugarcane bagasse with water is carried out under constant stirring or in a specially designed hydrolyser which ensures a smooth solid liquid contact so that less water and steam is used in the process.

Further, initially processing the sugarcane bagasse residue as per the process of the present invention is carried out at lower temperatures in the range of 120° C.-170° C. as compared to the industrially followed process where the processes are carried out at temperatures as high as in the range of 190° C.-200° C. Thus, in the present invention in terms of steam there is low energy utilization. Further the use of hazardous chemicals such as ammonia is avoided and there is no or less liquid and gaseous emission thus rendering the process of the present invention as environmental friendly.

The residue obtained after prehydrolysis is then treated with sulfite and at least one alkali or mixtures thereof preferably the alkali is a mixture of sodium carbonate and sodium hydroxide to obtain a residue having undissolved cellulose along with lignin rich liquor. The sulfite is sodium sulfite and the alkali is selected from sodium carbonate, sodium hydroxide or a mixture thereof preferably 5%-10% sodium sulfite, 1%-4% sodium carbonate and 7%-18% sodium hydroxide and wherein the process is carried out at a temperature in the range of 140° C.-180° C. preferably 160° C.-180° C. for 30-130 minutes preferably 90-120 minutes while maintaining the material to water ratio in the range of 1:3 to 1:8. The solid to liquid ratio is maintained in order to obtain concentrated black liquor containing dissolved lignin in the form of lignosulfonates. Thus, the lignin rich liquor obtained has more than 90% lignosulphonate purity and residue having undissolved pure cellulose has more than 30% undissolved pure cellulose. The lignin rich liquor and the residue having undissolved cellulose are then separated by pressing at high pressure and washing with minimum wash water and the recovery of lignosulphonate. The lignin recovered is in the range of 92-96% and residue having undissolved cellulose is in the range of 38%-40%

The above mentioned step of treating the residue obtained after prehydrolysis of sugarcane bagasse with sulfite and at least one alkali or mixtures thereof at a temperatures in the range of 140° C.-180° C. preferably 160° C.-180° C. for 30-130 minutes preferably 60-100 minutes while maintaining the material to water ratio in the range of 1:3 to 1:8 results in selectively solubilising the lignin component of the bagasse and insitu converting it into the lignosulphonate.

Further, in the above mentioned step, the lignin rich black liquor is then concentrated by ultra filtration, separating the high molecular weight lignosulphonate. The lignosulphonate thus obtained is suitable for application in the concrete and ceramic industry and plywood industries thus making the process of the present invention techno-commercially attractive.

In the aforesaid embodiment, the residue having undissolved cellulose is then further subjected to delignification carried out at a temperature in the range of 60° C.-140° C. preferably 80° C.-110° C., at a pH of 10-11 in the presence of 2-4% of sodium hydroxide and oxygen pressure at 3-5 kgs for 30-90 minutes by maintaining the material to liquid ratio in the range of 1:8 to 1:15. This step results in the separation of the remaining portion of lignin. The separation process of the remaining portion of lignin residue reduces the kappa number of the unbleached cellulose rich pulp so that the requirement of the bleaching agents is reduced thus leading to a reduction in the pollution load with respect to Chemical Oxygen Demand, color and toxicity.

The additional unit operation of oxygen delignification of residue having undissolved cellulose reduces the silica content in a cellulose rich pulp thus reducing the silica content from 0.06% to 0.045% which occurs due to further reduction. Further reduction of silica in the pulp is due to dissolution of the remaining silica in the pulp which occurs due to the dissolution of remaining silica at a pH level of above 10.

The step of delignification is the followed by treating the residue having undissolved cellulose with atleast one enzyme to obtain a cellulose rich pulp. The enzyme is selected from a class of hemicelluloses preferably xylanase having 7000 IU/ml at a dose of 0.01-0.1% and wherein the enzyme is added at a temperature of 30° C.-60° C. and a pH of 5-8 for 30-120 minutes and maintaining the material to liquid ratio of 1:8 to 1:15.

Thus, the cellulose rich unbleached pulp is then subjected to ECF bleaching sequence (DEpD) wherein the cellulose rich pulp is treated with elemental chlorine free bleaching agent such as Chlorine dioxide followed by sodium hydroxide and hydrogen peroxide which is then followed by further treatment with elemental chlorine free bleaching agent such as chlorine dioxide to obtain pure cellulose rich pulp.

Thus, the cellulose rich unbleached pulp is treated with an elemental chlorine free bleaching agent such as chlorine di-oxide solution in the range of 2 to 6%, preferably in the range of 3%-5% while maintaining the temperature in the range of 45° C.-80° C. for 30-90 minutes, the pH of 2-4 being maintained with 0.1% to 0.5% sulphuric acid and material to liquid ratio in the range of 1:20 to 1:30 followed by separating the treated residue.

The cellulose rich pulp is then further treated with 2% to 5% sodium hydroxide and 2%-4% hydrogen peroxide at a temperature in the range of 40° C.-80° C., material to liquid ratio of 1:8-1:12 for 30-120 minutes followed by separating the cellulosic pulp.

The cellulose rich pulp is then washed and filtered followed with the treatment with bleaching agents elemental chlorine free bleaching agent such as chlorine dioxide solution in the range of 1%-5% at a temperature in the range of 40° C.-90° C., material to liquor ratio of 1:8 to 1:12 for 120 to 240 minutes while maintaining the pH in the range of 3 to 4, to obtain pure cellulose rich pulp.

The pure cellulose rich pulp having high α-cellulose content of more than 95%, brightness value of more than 92% ISO and containing inorganic impurities less than 0.05% is then separated.

The intermittently obtained separated residue, residue have undissolved cellulose, cellulose rich pulp, pure cellulose rich pulp maybe washed with minimum water in order to minimize the effluent generated thereby reducing the pollution load on the effluent treatment plant or the discharge of the effluent thus making the process environment friendly. Further, washing with water or hot water removes the residual liquor impurities which are adhering to the residual material or the final product.

Further, the intermittently obtained residue, residue have undissolved cellulose, cellulose rich pulp, pure cellulose rich pulp is separated from the liquor by methods such as filtration, vaccum filtration, centrifugation, pressing or squeezing preferably under pressure or by employing any suitable means or technique.

Another embodiment of the present invention relates to a process for producing cellulose with low impurities, the process comprising of
  prehydrolyzing sugarcane bagasse to obtain a residue;
  treating the residue with sulfite and at least one alkali to obtain residue having undissolved cellulose along with lignin rich liquor;
  subjecting the residue having undissolved cellulose to delignification followed by addition of at least one enzyme to obtain a cellulose rich pulp;
  treating the cellulose rich pulp with an elemental chlorine free bleaching agent to obtain pure cellulose rich pulp; and
  separating the pure cellulose rich pulp having high α-cellulose content.

In another embodiment of the present invention, relates to a mixture for treatment of lignocellulose material, the mixture comprising sulfite and at least one alkali. The sulfite is selected from sodium sulfite and the alkali is selected from sodium carbonate, sodium hydroxide or a mixture thereof preferably the alkali is a mixture of sodium carbonate and sodium hydroxide.

In the present invention, industrial waste such as sugarcane bagasse residue is used and is converted into high quality cellulose. Thus, due to the use of such industrial waste material such as sugarcane bagasse the demand in cellulose based industries for wood resources would decreases which would then help curb deforestation. Moreover, in the process of the present invention there is recovery of useful derivatives such as xylan, lignosulphonate thus making the present invention sustainable.

Such sustainable processing of sugarcane bagasse into a spectrum of high quality value added chemicals which can be converted into industrially important products such as microcrystalline cellulose, cellulose esters, liquid fuels, commodity chemicals and industrial materials increases the sustainability of chemical and fuel production. Thus, the present invention can positively impact our environment and also provide economic benefits.

An advantage of the process of the present invention is that it is suitable for carrying it out at a small scale in laboratory, medium scale using the reactor having a 40-50 litre capacity, semi-commercial scale using a reactor having 1000 litre capacity and also for commercial production.

Thus, the present invention provides a simple, efficient and techno economical viable process for production of high purity cellulose pulp with negligible impurities of undesired inorganic components such as silica. The present invention further describes the process consisting of various unit operations such as depithing of the bagasse for efficient removal of pith (an undesired component of bagasse) which is present upto 40%, and responsible for higher consumption of chemical, presence of high silica content thus having an adverse effect on the quality of the product, finally the cellulose. The other unit operations includes prehydrolysis of bagasse under optimized conditions, alkaline pulping using the developed process for removal of lignin and silica, oxygen delignification process which also helps in removal of lignin and silica from the cellulose rich pulp followed by elemental chlorine free bleaching incorporating the use of xylnase enzyme pretreatment followed by two stage chlorine dioxide and single stage alkaline and peroxide treatment. All these unit operations help in reduction of the silica from the cellulosic pulp at each stage of unit operation finally producing the high purity cellulose which contains negligible amount of silica thus making the cellulose and value added products obtained industrially useful.

Thus, the present invention relates to the development of a novel process in which the unit operations for production of cellulose from silica rich bagasse, are designed in such a way that the silica gets reduced at every stage of process and the cellulose finally obtained is of highest purity and almost devoid of silica. The high purity cellulose thus obtained finds applications in value added industrially useful products and also results in the recovery of other two major constituents of bagasse namely hemicellulose and lignin.

In another embodiment of the present invention, provides a process for producing cellulose with alpha-cellulose content of more than 95%, inorganic impurities less than 0.03% from sugarcane bagasse residue comprising subjecting the sugarcane bagasse residue to prehydrolysis to ensure smooth material liquid contact at a temperature in the range of 120° C.-170° C. at a material to liquid ratio of 1:6 to 1:10 for 60 to 215 minutes followed by vaccum filtration and separation of more than 90% hemicelluloses with a concentration of 30-40g/l of xylan and recovering 76%-78% of residue;

treating the residue with 6%-10% sodium sulfite, 1%-4% sodium carbonate, 7%-12% sodium hydroxide at a temperature in the range of 130° C.-170° C. for 60-120 minutes maintaining the material to water ratio in the range of 1:4 to 1:7 to selectively solubilise the lignin component of the bagasse and insitu converting it to lignosulphonate to obtain a lignin rich liquor along with residue having undissolved cellulose which is then separated by passing the lignin rich liquor through ultra filtration and recovering the high molecular weight lignosulphonate;

subjecting the residue having undissolved cellulose to further delignification at a temperature in the range of 80° C.-100° C. at a pH of above 10 with 2%-4% w/w sodium hydroxide and oxygen pressure of 3-5 kg for 50-70 minutes and a material to liquid ratio in the range of 1:10 to 1:13;

treating the residue having undissolved cellulose with xylnase having 7000 IU/ml with enzyme dose of 0.03% to 0.1% at a temperature in the range of 40° C.-60° C., pH 5-8 for 30-120 minutes maintaining the material to liquid ratio at 1:10 followed by separating the cellulose rich pulp;

treating the cellulose rich pulp with 3-7% chlorine dioxide, 2%-4% sodium hydroxide and 2-3% hydrogen peroxide maintaining the temperature at 50° C.-80° C., pH 2-4, material to liquid ratio of 1:30 for 44-180 minutes to obtain pure cellulose rich pulp separating the pure cellulose rich pulp having more than 95% α-cellulose content, brightness value of more than 92% ISO and less than 0.03% inorganic impurities.

In an embodiment of the present invention, steps of the process of the present invention maybe carried out in an available bioreactor in a continuous manner or as separate unit operations carried out sequentially.

In an embodiment of the present invention, steps of the process of the present invention maybe carried out in a specially designed bioreactor or a particular unit of the bioreactor specifically designed.

EXPERIMENTAL DATA

Ash test as per standard TAPPI Method T-211 on 93 was carried out. The results obtained showed that the inorganic impurities such as that of silica was less than 0.05%.

The sugarcane bagasse used in the present invention is from sugarcane which has been obtained from Karnataka.

Example 1

400 kg of depithed sugarcane bagasse having 10% moisture with less than 10% pith was washed with water to remove adhered inorganic impurities such as silica and fed in to a digester. The sugarcane bagasse was prehydrolyzed with water which was added to the digester in the ratio of 1:10 and steam was allowed inside to maintain the temperature of 160° C. and maintained for 150 minutes. It was then cooled to a temperature of 80° C. The prehydrolyzed sugarcane bagasse was then fed in to a screw press having a filteration device to separate the hemicellulose and residue. 63.0 kgs of dry hemicelluloses was obtained in the form of a dilute solution and 295 kgs residue was obtained which was then washed with hot demineralized water.

295 kg of the washed residue was then charged in to digester, 32 kgs of sodium hydroxide, 50 kgs of sodium sulfite and 12 kgs sodium carbonate as $Na_2O$ were added and the pH of the solution was maintained at 9. Steam was allowed inside to maintain the temperature at 160° C. for 1.0 hour. It was then cooled to a temperature of 80° C. to obtain residue having undissolved cellulose along with lignin rich liquor which was then fed in to screw press to separate the dilute lignin rich liquor having lignosufonate and residue having undissolved cellulose. 134 kg of dry lignosufonate in the form of dilute solution and about 120 kgs of residue having undissolved cellulose was obtained.

120 kg residue having undissolved cellulose was washed twice with hot water to obtain black liquor free pulp/residue having undissolved cellulose which was again sent to a digester where 24 kgs of sodium hydroxide was added and 4.0 kgs oxygen pressure was maintained inside the reactor at a the temperature of 80° C. for 1.0 hour. It was then passed through the screw press having filteration device, the effluent separated and washed the unbleached pulp/residue having undissolved cellulose with dimineralized water. The washed pulp/residue having undissolved cellulose was sent to bleaching reactor, 0.2 kg of xylanase enzyme was added and the temperature was maintained at 50° C. for two hours. It was then filtered and the cellulose rich pulp was washed with demineralised water. The washed cellulose rich pulp was then sent to a bleaching reactor, the pH of the solution was maintained by adding sulphuric acid, and 7.0 kgs chlorine dioxide was then added (resulting from the mixture of chemicals sodium chlorite, sodium acetate, glacial acetic acid in specific ratio). The temperature was maintained at 50° C. for about 45 minutes. The effluent was filtered and pulp was washed with demineralised water.

The washed pulp was then sent to a bleaching reactor, added 4.0 kgs Sodium hydroxide, 3.0 kgs hydrogen peroxide was added the temperature was maintained at 70° C. for about 1.0 hour, the effluent was filtered and the pulp was washed with demineralised water. The washed pulp was then sent to a bleaching reactor where the pH of the solution was maintained by adding sulphuric acid. Further, 3.0 kgs chlorine dioxide(resulting from the mixture of chemicals sodium chlorite, sodium acetate, glacial acetic acid in specific ratio) was added and the temperature was maintained at 80° C. degree for 2 hours, the effluent was filtered and then pure cellulose pulp was washed with demineralised water. 105 kgs of pure cellulose pulp was obtained which has less than 0.05% silica content.

Example 2

240 kgs of depithed sugarcane bagasse containing with less than 15% pith was washed with water to remove adhered inorganic impurities such as silica and fed in to a digester. The sugarcane bagasse was prehydrolyzed with water which was added to the digester in the ratio of 1:8 and steam was allowed inside to maintain the temperature at 165° C. and maintained for 2.0 hours. It was then cooled to a temperature of 90° C. The prehydrolyzed sugarcane bagasse was then fed in to screw press having a filteration device to separate the hemicelluloses and residue. 45.0 kgs of dry hemicelluloses was obtained in the form of a dilute solution and 190 kgs of residue was obtained which was washed with hot demineralised water.

190 kgs of washed residue was then charged in to digester 21 kg of sodium hydroxide, 32 kgs of sodium sulfite and 7.0 kgs sodium carbonate as $Na_2O$ was added and pH of the solution was maintained at 10. Steam was allowed inside to be maintained at a temperature of 165° C. and maintained for 1.0 hour. It was then cooled to the temperature of 90° C. to obtain residue having undissolved cellulose along with lignin rich liquor which was then fed in to a screw press to separate the dilute lignosufonate and residue having undissolved cellulose. 96 kgs of dry lignosufonate in the form of dilute solution was obtained and 82 kg of residue having undissolved cellulose.

82.0 kgs of residue having undissolved cellulose was washed twice with hot water to obtain black liquor free pulp/residue having undissolved cellulose which was again sent to digester where 16.4 kgs of sodium hydroxide was added and 4.0 kgs oxygen pressure was maintained inside the reactor at a temperature of 85° C. for 1.0 hour. It was then passed through the screw press having a filteration device and the effluent was separated and unbleached pulp/ having undissolved cellulose was washed with demineralised water. The washed pulp/having undissolved cellulose was sent to the bleaching reactor, 0.15 kg of xylanase enzyme was added and the temperature was maintained at 55° C. for two hours. It was then filtered and the cellulose rich pulp was washed with demineralised water. The washed cellulose rich pulp sent to a bleaching reactor, the pH of the solution was maintained by adding sulphuric acid, and 5.0 kgs chlorine dioxide was then added (resulting from the mixture of chemicals sodium chlorite, sodium acetate, glacial acetic acid in specific ratio). The temperature was maintained at 55° C. for 50 minutes. The effluent was, filtered and the pulp was washed with demineralised water.

The washed pulp was sent to a bleaching reactor, 1.7 kg Sodium hydroxide, 1.5 kgs hydrogen peroxide was added and temperature was maintained at 75° C. for 1.5 hours. The effluent was filtered washed the pulp was washed with demineralised water. The washed pulp was then sent to a bleaching reactor, the pH of the solution was maintained by adding sulphuric acid. Further, 2.5 kgs chlorine dioxide was added (resulting from the mixture of chemicals sodium chlorite, sodium acetate, glacial acetic acid in specific ratio) and the temperature was maintained at 85° C. degree for 2.5 hours. The effluent was filtered and the pure cellulose rich pulp was washed with demineralised water. 75 kgs of pure cellulose rich pulp on a dry basis having less than silica content 0.05% was obtained.

Example 3

100 kg of depithed bagasse having 10% moisture with around 5% pith content was washed with water to remove adhered inorganic impurities such as silica and fed to a digester. The sugarcane bagasse was prehydrolysed with water which was added to digester in the ratio of 1:8, steam was allowed inside to maintain the temperature of 170° C. and was maintained 3.0 hours. It was then cooled to a temperature of 100° C. The pre hydrolyzed material is fed in to a screw press having a filteration device to separate the dissolved hemicelluloses and residue in the form of solid biomass. 21 kgs (bone dried) dry hemicellulose was obtained in the form of dilute solution. 69.0 kgs residue was obtained which was washed with hot demineralised water.

68 kg washed residue was charged in to the digester, 7.0 kgs of sodium hydroxide, 14 kgs of sodium sulfite and 3.5 kgs sodium carbonate as $Na_2O$ were added, the pH of the solution was maintained at 11. Steam was allowed inside to maintain the temperature at 170° C. and maintained for 1.30 hours. It was then cooled to a temperature of 100° C. to obtain residue having undissolved cellulose along with lignin rich liquor which was then fed in to screw press to separate the dilute lignin rich liquor having lignosufonate and the residue having undissolved cellulose. 50 kgs of dry lignosufonate in the form of dilute solution and 33 kgs of residue having undissolved cellulose was obtained.

120 kg of residue having undissolved cellulose was washed twice with hot water to obtain black liquor free pulp/residue having undissolved cellulose which was again sent to digester where 24 kgs of sodium hydroxide was added and 4.0 kgs oxygen pressure was maintained inside the reactor at the temperature of 90° C. for 1.0 hour. It was the passed through the screw press having a filteration device, the effluent separated and washed the unbleached pulp/residue having undissolved cellulose with demineralised water. The washed pulp/residue having undissolved cellulose was sent to the bleaching reactor and 0.005 kg of xylanase enzyme was added and the temperature was maintained at 60° C. for two hours. It was then filtered and cellulose rich pulp was washed with demineralised water. The washed cellulose rich pulp was sent to a bleaching reactor, the pH of the solution was maintained by adding sulphuric acid and 1.9 kgs of chlorine dioxide (resulting from the mixture of chemicals sodium chlorite, sodium acetate, glacial acetic acid in specific ratio) was added the temperature was maintained 60° C. for 60 minutes, the effluent was filtered and pulp was washed with demineralised water.

The washed pulp was then sent to bleaching reactor, 0.6 kg Sodium Hydroxide, 0.6 Kg hydrogen peroxide was added and the temperature was maintained in the range of 80° C. for 2.0 hours. The effluent was filtered and the pulp was washed with demineralised water. The washed pulp was then sent to bleaching reactor the pH of the solution was maintained by adding sulphuric acid and 0.6 kg chlorine dioxide (resulting from the mixture of chemicals sodium chlorite, sodium acetate, glacial acetic acid in specific ratio) was added and the temperature was maintained at 90° C. degree for about 3 hours. The effluent was filtered and then pure cellulose rich pulp was washed with demineralised water. 29 kgs of pure cellulose rich pulp was obtained which has less than 0.05% silica content.

The forgoing description of the invention has been set merely to illustrate the invention and is not intended to be limiting. Since, modifications of the disclosed embodiments incorporating the spirit and substance of the invention may occur to a person skilled in the art, the invention should be construed to include everything within the scope of the disclosure.

The invention claimed is:
1. A process for producing cellulose from sugarcane bagasse, the process comprising:
   treating prehydrolyzed sugarcane bagasse in the absence of anthraquinone with mixture of sulfite and at least one alkali to obtain a residue having undissolved cellulose along with lignin rich liquor, the prehydrolyzed sugarcane bagasse is obtained by treating sugarcane bagasse residue with water at a temperature in a range of 120° C.-170° C.;

subjecting the residue having undissolved cellulose to delignification at a temperature in a range of 60° C.-140° C., at a pH of 10-11 in the presence of 2-4% of sodium hydroxide and oxygen pressure at 3-5 kgs; and after the delignification, adding at least one enzyme to obtain a cellulose rich pulp having less than 0.05% of inorganic impurities including silica;

wherein the cellulose rich pulp is suitable for making microcrystalline cellulose or cellulose esters.

2. The process as claimed in claim 1, wherein the sulfite is sodium sulfite and the alkali is selected from sodium carbonate, sodium hydroxide or mixture thereof.

3. The process as claimed in claim 2, comprising 5%-10% sodium sulfite, 1%-4% sodium carbonate and 7%-18% sodium hydroxide and wherein the process is carried out at a temperature in the range of 140° C. -180° C.

4. The process as claimed in claim 1, comprising:
treating the cellulose rich pulp with a bleaching agent to obtain a pure cellulose rich pulp; and
separating the pure cellulose rich pulp having a high α-cellulose content.

5. The process as claimed in claim 1, wherein the enzyme is selected from a class of hemicelluloses including xylanase, and wherein the enzyme is added at a temperature of 30° C.-60° C. and pH of 5-8.

6. The process as claimed in claim 4, comprising adding an elemental chlorine free bleaching agent followed by adding 2%-5% sodium hydroxide and 2-4% hydrogen peroxide, further followed by treatment with elemental free chlorine bleaching agent to the cellulose rich pulp to obtain the pure cellulose rich pulp.

7. The process as claimed in claim 4, wherein the bleaching agent is selected from chlorine dioxide, and the bleaching agent is added at a temperature in a range of 40° C.-90° C. at a pH of 2-4.

* * * * *